United States Patent
Fishel et al.

(10) Patent No.: US 9,477,909 B2
(45) Date of Patent: Oct. 25, 2016

(54) OBJECT INVESTIGATION AND CLASSIFICATION

(71) Applicant: SYNTOUCH, LLC, Los Angeles, CA (US)

(72) Inventors: Jeremy A. Fishel, Fullerton, CA (US); Gerald E. Loeb, South Pasadena, CA (US)

(73) Assignee: SYNTOUCH, LLC, Los Angeles, CA (US)

( * ) Notice: Subject to any disclaimer, the term of this patent is extended or adjusted under 35 U.S.C. 154(b) by 407 days.

(21) Appl. No.: 14/151,625

(22) Filed: Jan. 9, 2014

(65) Prior Publication Data

US 2014/0195195 A1    Jul. 10, 2014

Related U.S. Application Data

(60) Provisional application No. 61/750,674, filed on Jan. 9, 2013.

(51) Int. Cl.
*G06F 15/18* (2006.01)
*G06K 9/62* (2006.01)
*G01B 21/30* (2006.01)

(52) U.S. Cl.
CPC .............. *G06K 9/6277* (2013.01); *G01B 21/30* (2013.01)

(58) Field of Classification Search
CPC .................................. G01B 21/30; G01B 9/00
USPC .......................................... 706/12, 45, 62, 20
See application file for complete search history.

(56) References Cited

U.S. PATENT DOCUMENTS

| | | | |
|---|---|---|---|
| 6,601,457 B2 | 8/2003 | Li et al. | |
| 7,658,110 B2 | 2/2010 | Fukukita | |
| 7,878,075 B2 | 2/2011 | Johansson et al. | |
| 8,181,540 B2 | 5/2012 | Loeb et al. | |
| 8,272,278 B2 | 9/2012 | Loeb et al. | |
| 2011/0075920 A1* | 3/2011 | Wu | G06K 9/4638 382/160 |
| 2011/0157088 A1* | 6/2011 | Motomura | G06F 3/014 345/174 |
| 2013/0202173 A1* | 8/2013 | Buckler | G06T 7/0012 382/131 |

OTHER PUBLICATIONS

Adams, M.J. et al 2013. Finger pad friction and its role in grip and touch. Journal of the Royal Society Interface, 10 (80), 20 pages.
Adams, R. A., et al. 2013. Predictions not commands: active inference in the motor system. Brain Structure & Function, 218(3), 611-643.

(Continued)

*Primary Examiner* — David Vincent
(74) *Attorney, Agent, or Firm* — McDermott Will & Emery LLP

(57) ABSTRACT

An object investigation and classification system may include an object test system, a data storage system, and a data processing system. The object test system may receive a command to perform at least one action with a test object, perform the at least one action with the test object, and return test information indicative of at least one percept resulting from the at least one action. The data storage system may contain an experience database containing data indicative of multiple classifications and, for each classification, at least one action that was performed with at least one previously-observed reference object having this classification, and at least one percept value that is based in whole or in part on the test information resulting from the at least one action.

33 Claims, 4 Drawing Sheets

(56) References Cited

OTHER PUBLICATIONS

Bergmann Tiest, W.M. et al. 2006. Analysis of haptic perception of materials by multidimensional scaling and physical measurements of roughness and compressibility. Acta Psychologica, 121(1), 1-20.
Chu, V.I. et al. 2013. Using Robotic Exploratory Procedures to Learn the Meaning of Haptic Adjectives. In Proc. Robotics and Automation (ICRA), 2013 IEEE International Conference on, pp. 3048,3055, May 6-10, 2013.
Civille, G.V. et al. 1990. Development of terminology to describe the handfeel properties of paper and fabrics. Journal of Sensory Studies, 5(1), 19-32.
Cohn, D.A. et al. 1996. Active Learning with Statistical Models. Journal of Artificial Intelligence Research, 4, 129-145.
Culbertson, H. et al. 2014. One hundred data-driven haptic texture models and open-source methods for rendering on 3D objects. Haptics Symposium (HAPTICS), 2014 IEEE, 319-325.
Dahiya, R S. et al. 2010. Tactile Sensing—From Humans to Humanoids. IEEE Transactions on Robotics 26 (1): 1-20.
De Boissieu, F. et al. 2009. Tactile Texture Recognition with a 3-Axial Force MEMS Integrated Artificial Finger. In Proc. Robotics: Science and Systems, 49-56.
Derler, S. et al. 2007. Tribology of human skin and mechanical skin equivalents in contact with textiles. Wear, 263 (7), 1112-1116.
Dong, Y. et al. 2013. A simple model of mechanotransduction in primate glabrous skin. Journal of Neurophysiology, 109(5), 1350-1359.
Fishel, J A, et al. 2012. Bayesian Exploration for Intelligent Identification of Textures. Frontiers in Neurorobotics 6 (4): 1-20.
Gibson, J. J. 1986. "The Theory of Affordances," Chapter 8 in Perceiving, Acting, and Knowing, eds. Robert Shaw and John Bransford, ISBN 0-470-99014-7, pp. 127-133.
Giguere, P, 2011. A Simple Tactile Probe for Surface Identification by Mobile Robots. IEEE Transactions on Robotics 27 (3): 534-544.
Goudarzi, A. et al. 2014. A Comparative Study of Reservoir Computing for Temporal Signal Processing. Preprint Jan. 2014, available at http://arxiv-web3.library.cornell.edu/pdf/1401.2224v1.pdf.
Hosoda, K. et al. 2006. Anthropomorphic Robotic Soft Fingertip with Randomly Distributed Receptors. Robotics and Autonomous Systems 54 (2): 104-109.
Howe, R D. 1994. Tactile Sensing and Control of Robotic Manipulation. Advanced Robotics 8 (3): 245-261.
Hsiao, K. et al. 2010. Task-driven tactile exploration. Proceedings of Robotics: Science and Systems Conference, Jun. 2010.
Hu, J. 2006. Characterization of sensory comfort of apparel products.. Ph.D. Thesis, The Hong Kong Polytechnic University.
Hu, J.Y. et al. 2006. Fabric Touch Tester: Integrated evaluation of thermal—mechanical sensory properties of polymeric materials. Polymer Testing, 25(8), 1081-1090.
Jain, A.K. et al. 2000. Statistical Pattern Recognition: A Review. IEEE Transactions on Pattern Analysis and Machine Intelligence 22 (1): 4-37.
Jamali, N. et al. 2011. "Majority Voting: Material Classification by Tactile Sensing Using Surface Texture." IEEE Transactions on Robotics 27 (3): 508-521.
Johansson, R.S. et al. 1979. Tactile Sensibility in the Human Hand: Relative and Absolute Densities of Four Types of Mechanoreceptive Units in Glabrous Skin. Journal of Physiology 286 (1): 283.

Jones, L.A. et al. 2006. Human Hand Function. New York, NY: Oxford University Press, USA, pp. 76-99.
Klöcker, A. et al. 2013. Physical Factors Influencing Pleasant Touch during Tactile Exploration. PLoS ONE, 8(11).
Lederman, S.J. et al. 1987. Hand Movements: a Window Into Haptic Object Recognition. Cognitive Psychology 19: 342-368.
Lee, M.H. et al. 1999. "Tactile Sensing for Mechatronics— a State of the Art Survey." Mechatronics 9: 1-31.
Lin, C.H. et al. 2009. Signal Processing and Fabrication of a Biomimetic Tactile Sensor Array with Thermal, Force and Microvibration Modalities. In Proc. IEEE International Conference on Robotics and Biomimetics, 129-134.
Loeb, G.E. et al. 2011. Understanding Haptics by Evolving Mechatronic Systems. Progress in Brain Research 192: 129-144.
Mukaibo, Y. et al. 2005. Development of a Texture Sensor Emulating the Tissue Structure and Perceptual Mechanism of Human Fingers. In Proc. IEEE International Conference on Robotics and Automation, 2565-2570. IEEE.
Najemnik, J. et al. 2005. Optimal eye movement strategies in visual search. Nature, 434(7031), 387-391.
Nicholls, H.R. et al. 1989. A Survey of Robot Tactile Sensing Technology. International Journal of Robotics Research 8 (3): 3-30.
Oddo, C.M. et al. 2011. Roughness Encoding for Discrimination of Surfaces in Artificial Active-Touch. IEEE Transactions on Robotics 27 (3): 522-533.
Sinapov, J. et al. 2010. The Boosting Effect of Exploratory Behaviors. In Proc. Association for the Advancement of Artificial Intelligence, 1613-1618.
Sinapov, J. et al. 2011. Vibrotactile Recognition and Categorization of Surfaces by a Humanoid Robot. IEEE Transactions on Robotics 27 (3): 488-497.
Su, Z. et al. 2012. Use of Tactile Feedback to Control Exploratory Movements to Characterize Object Compliance. Frontiers in Neurorobotics 6(7): 1-12.
Szary, J. et al. 2011. What makes a brain smart? reservoir computing as an approach for general intelligence. In Proceedings of the 4th International Conference on Artificial General Intelligence, pp. 407-413, 2011.
Tada, Y. et al. 2004. "Sensing Ability of Anthropomorphic Fingertip with Multi-Modal Sensors." In Proc. IEEE International Conference on Intelligent Robots and Systems, 1005-1012.
Tomlinson, S.E. et al. 2007. Review of the frictional properties of finger-object contact when gripping. Proceedings of the Institution of Mechanical Engineers, Part J: Journal of Engineering Tribology, 221(8), 841-850.
Vallbo, Å.B. et al. 1978. The Tactile Sensory Innervation of the Glabrous Skin of the Human Hand. In Active Touch, the Mechanism of Recognition of Objects by Manipulation, edited by G Gordon, 29-54. Oxford: Pergamon Press Ltd.
Weber, A.I. et al. 2013. Spatial and temporal codes mediate the tactile perception of natural textures. Proceedings of the National Academy of Sciences, 110(42), 17107-17112.
Aerotech. (Date unknown.) ANT95-L Series: Mechanical Bearing. (Include information on ANT95-75-L) (Aerotech, Pittsburgh, PA) Downloaded May 22, 2014 from http://www.aerotech.com/media/114414/ant95-l.pdf.
SDL ATLAS. (Date unknown.) Fabric Touch Tester product brochure. (SDL ATLAS, Rock Hill, SC). Downloaded May 22, 2014 from http://www.sdlatlas.com/media/manuals/eng_FTT-ENG(20140123).pdf.

* cited by examiner

OBJECT INVESTIGATION AND CLASSIFICATION

CROSS-REFERENCE TO RELATED APPLICATION

This application is based upon and claims priority to U.S. provisional patent application 61/750,674, entitled "Apparatus and Method for Characterizing, Discriminating, and Identifying Objects Based on Tactile Properties," filed Jan. 9, 2013. The entire content of this application is incorporated herein by reference.

STATEMENT REGARDING FEDERALLY SPONSORED RESEARCH

This invention was made with government support under Contract No. D11PC20121, awarded by the Defense Advanced Research Projects Agency (DARPA). The government has certain rights in the invention.

BACKGROUND

Touch may require movements to be made with fingertips in order to sense information about what the fingers are touching. The nature of these movements may be optimized to extract the tactile properties of an object that may be useful for identifying the object. Experimental psychologists have observed a number of useful types of exploratory movements that humans make when identifying objects by touch, such as hefting, enclosing, applying pressure, and sliding. (Lederman, S J, and R L Klatzky. 1987. "Hand Movements: a Window Into Haptic Object Recognition." Cognitive Psychology 19: 342-368.). However, even within these discrete sets of movements, there may be many ways in which these movements can be executed to collect information. For instance, different combinations of forces and sliding trajectories could be made when performing a sliding movement. Given the large number of possible movements and variations in parameters, it may be impractical to perform every possible movement to collect every piece of information before identifying what is being touched. Similar problems may arise during any type of diagnostic task when it may be impractical to collect all information before making a decision. For example, the definitive diagnosis of a disease given an initial set of symptoms could benefit from a very large number of possible tests, each of which takes a significant amount of time and money to perform. Physicians use a subjective process called differential diagnosis to estimate the probability of each possible diagnosis and the potential of each available test to differentiate among them. It would be advantageous to have an objective method to determine the most efficient sequence of tests to arrive at a final diagnosis.

Human skin contains a variety of neural transducers that sense mechanical strain, vibrations, and thermal information (Jones, L A, and S J. Lederman. 2006. Human Hand Function. New York, N.Y.: Oxford University Press, USA.; Vallbo, A B, and R S Johansson. 1984. "Properties of Cutaneous Mechanoreceptors in the Human Hand Related to Touch Sensation." Human Neurobiology 3 (1): 3-14.). The skin and its sensory transducers are highly evolved and specialized in structure, and the glabrous skin found on the palmar surface of the human hand, and in particular the fingertip, may possess a higher density of cutaneous receptors than the hairy skin on the rest of the body (Vallbo, Å B, and R S Johansson. 1978. "The Tactile Sensory Innervation of the Glabrous Skin of the Human Hand." In Active Touch, the Mechanism of Recognition of Objects by Manipulation, edited by G Gordon, 29-54. Oxford: Pergamon Press Ltd.; Johansson, R S, and Å B Vallbo. 1979. "Tactile Sensibility in the Human Hand: Relative and Absolute Densities of Four Types of Mechanoreceptive Units in Glabrous Skin." Journal of Physiology 286 (1): 283.). A device that mimics these sensory capabilities has been described in a form factor that has size, shape and mechanical properties similar to a human fingertip (U.S. Pat. Nos. 7,658,110, 7,878,075, 8,181,540 and 8,272,278). Other tactile sensors designed to replicate human touch have been described in a number of literature reviews covering several decades of research (Nicholls, H R, and M H Lee. 1989. "A Survey of Robot Tactile Sensing Technology." International Journal of Robotics Research 8 (3): 3-30.; Howe, R D. 1994. "Tactile Sensing and Control of Robotic Manipulation." Advanced Robotics 8 (3): 245-261.; Lee, M H, and H R Nicholls. 1999. "Tactile Sensing for Mechatronics—a State of the Art Survey." Mechatronics 9: 1-31.; Dahiya, R S, G Metta, M Valle, and G Sandini. 2010. "Tactile Sensing—From Humans to Humanoids." IEEE Transactions on Robotics 26 (1): 1-20.).

Another approach is artificial texture recognition with tactile sensors (Tada, Y, K Hosoda, and M Asada. 2004. "Sensing Ability of Anthropomorphic Fingertip with Multi-Modal Sensors." In Proc. IEEE International Conference on Intelligent Robots and Systems, 1005-1012.; Mukaibo, Y, H Shirado, M Konyo, and T Maeno. 2005. "Development of a Texture Sensor Emulating the Tissue Structure and Perceptual Mechanism of Human Fingers." In Proc. IEEE International Conference on Robotics and Automation, 2565-2570. IEEE.; Hosoda, K, Y Tada, and M Asada. 2006. "Anthropomorphic Robotic Soft Fingertip with Randomly Distributed Receptors." Robotics and Autonomous Systems 54 (2): 104-109.; de Boissieu, F, C Godin, B Guilhamat, D David, C Serviere, and D Baudois. 2009. "Tactile Texture Recognition with a 3-Axial Force MEMS Integrated Artificial Finger." In Proc. Robotics: Science and Systems, 49-56.; Sinapov, J, and A Stoytchev. 2010. "The Boosting Effect of Exploratory Behaviors." In Proc. Association for the Advancement of Artificial Intelligence, 1613-1618.; Giguere, P, and G Dudek. 2011. "A Simple Tactile Probe for Surface Identification by Mobile Robots." IEEE Transactions on Robotics 27 (3): 534-544.; Oddo, C M, M Controzzi, L Beccai, C Cipriani, and M C Carrozza. 2011. "Roughness Encoding for Discrimination of Surfaces in Artificial Active-Touch." IEEE Transactions on Robotics 27 (3): 522-533.; Jamali, N, and C Sammut. 2011. "Majority Voting: Material Classification by Tactile Sensing Using Surface Texture." IEEE Transactions on Robotics 27 (3): 508-521.; Sinapov, J, V Sukhoy, R Sahai, and A Stoytchev. 2011. "Vibrotactile Recognition and Categorization of Surfaces by a Humanoid Robot." IEEE Transactions on Robotics 27 (3): 488-497.; Chu, V, I McMahon, L Riano, C G McDonald, Q He, J M Perez-Tejada, M Arrigo, et al. 2013. "Using Robotic Exploratory Procedures to Learn the Meaning of Haptic Adjectives." In Proc. IEEE International Conference on Robotics and Automation.). The sliding movements humans make when identifying surface texture (Lederman, S J, and R L Klatzky. 1987. "Hand Movements: a Window Into Haptic Object Recognition." Cognitive Psychology 19: 342-368.) may be executed with these sensors over a number of textures to identify which characteristics make them unique. Various approaches to producing these movements have been explored, including using anthropomorphic hands (Tada, Y, K Hosoda, and M Asada. 2004. "Sensing Ability of Anthropomorphic Fingertip with Multi- Modal Sensors." In Proc. IEEE International Conference on Intelligent Robots and Systems, 1005-1012.; Hosoda, K, Y Tada, and M Asada. 2006. "Anthropomorphic Robotic Soft Fingertip with Randomly Distributed Receptors." Robotics and Autonomous Systems 54 (2): 104-109.; Oddo, C M, M Controzzi, L Beccai, C Cipriani, and M C Carrozza. 2011. "Roughness Encoding for Discrimination of Surfaces in Artificial Active-Touch." IEEE Transactions on Robotics 27 (3): 522-533.; Jamali, N, and C Sammut. 2011. "Majority Voting: Material Classification by Tactile Sensing Using Surface Texture." IEEE Transactions on Robotics 27 (3): 508-521.; Chu, V, I McMahon, L Riano, C G McDonald, Q He, J M Perez-Tejada, M Arrigo, et al. 2013. "Using Robotic Exploratory Procedures to Learn the Meaning of Haptic Adjectives." In Proc. IEEE International Conference on Robotics and Automation.), 2-axis plotting machines (de Boissieu, F, C Godin, B Guilhamat, D David, C Serviere, and D Baudois. 2009. "Tactile Texture Recognition with a 3-Axial Force MEMS Integrated Artificial Finger." In Proc. Robotics: Science and Systems, 49-56.), robotic arms (Sinapov, J, V Sukhoy, R Sahai, and A Stoytchev. 2011. "Vibrotactile Recognition and Categorization of Surfaces by a Humanoid Robot." IEEE Transactions on Robotics 27 (3): 488-497.), or manual sliding (Giguere, P, and G Dudek. 2011. "A Simple Tactile Probe for Surface Identification by Mobile Robots." IEEE Transactions on Robotics 27 (3): 534-544.). Previous studies employed a fixed exploration sequence for collecting data, which, after processing, was fed into a machine learning classifier that sought to identify the texture. One exception was (Jamali, N, and C Sammut. 2011. "Majority Voting: Material Classification by Tactile Sensing Using Surface Texture." IEEE Transactions on Robotics 27 (3): 508-521.), who repeated the same sliding movement until the classification reached a desired confidence.

Using additional exploratory movements has been demonstrated to improve performance (Sinapov, J, V Sukhoy, R Sahai, and A Stoytchev. 2011. "Vibrotactile Recognition and Categorization of Surfaces by a Humanoid Robot." IEEE Transactions on Robotics 27 (3): 488-497.). However, executing every possible movement to gain all information about an object may be impractical, so these systems were restricted to a small number of preprogrammed exploratory movements. This approach may only provide marginal performance accuracies when using a small number of highly distinctive surfaces that would be trivial for a human observer to discriminate. Examples of classification performance in previous literature include: 62% over 10 textures (de Boissieu, F, C Godin, B Guilhamat, D David, C Serviere, and D Baudois. 2009. "Tactile Texture Recognition with a 3-Axial Force MEMS Integrated Artificial Finger." In Proc. Robotics: Science and Systems, 49-56.), 89.9-94.6% over 10 textures (Giguere, P, and G Dudek. 2011. "A Simple Tactile Probe for Surface Identification by Mobile Robots." IEEE Transactions on Robotics 27 (3): 534-544.), 95% over 20 textures (Sinapov, J, V Sukhoy, R Sahai, and A Stoytchev. 2011. "Vibrotactile Recognition and Categorization of Surfaces by a Humanoid Robot." IEEE Transactions on Robotics 27 (3): 488-497.), 97.6% over 3 textures (Oddo, C M, M Controzzi, L Beccai, C Cipriani, and M C Carrozza. 2011. "Roughness Encoding for Discrimination of Surfaces in Artificial Active-Touch." IEEE Transactions on Robotics 27 (3): 522-533.), and 95% over 8 textures (Jamali, N, and C Sammut. 2011. "Majority Voting: Material Classification by Tactile Sensing Using Surface Texture." IEEE Transactions on Robotics 27 (3): 508-521.).

Loeb et al., 2011, (Loeb, G E, G A Tsianos, J A Fishel, N Wettels, and S Schaal. 2011. "Understanding Haptics by Evolving Mechatronic Systems." Progress in Brain Research 192: 129-144.), suggested the general desirability of selecting exploratory movements incrementally according to the most likely identity of the object being explored but, provided no examples or methods to do so.

SUMMARY

An object investigation and classification system may include an object test system, a data storage system, and a data processing system. The object test system may receive a command to perform at least one action with a test object, perform the at least one action with the test object, and return test information indicative of at least one percept resulting from the at least one action. The data storage system may contain an experience database containing data indicative of multiple classifications and, for each classification, at least one action that was performed with at least one previously-observed reference object having this classification, and at least one percept value that is based in whole or in part on the test information resulting from the at least one action. The data processing system may: a) for each of multiple different classifications, compute or receive an initial prior probability that a test object falls within the classification; b) determine at least one action that should be performed with the test object to obtain at least one percept about the test object that is likely to enable the classification of the test object to be more accurately determined based on the initial prior probabilities and the data within the experience database; c) cause the object test system to perform the at least one action with the test object; d) receive test information from the object test system indicative of at least one percept resulting from the at least one action with the test object; e) compute at least one percept value; f) for each of multiple different classifications, determine a posterior probability that the test object falls within the classification based on the initial prior probability, the at least one percept value, and data within the experience database; g) determine whether any of the posterior probabilities meets or exceeds a threshold; h) if none of the posterior probabilities meet or exceed the threshold, repeat b) through i), substituting the posterior probabilities determined in f) for the initial prior probabilities in b); and/or i) when one or more of the posterior probabilities meets or exceeds the threshold, output information indicative of one or more of the classifications that correspond to the one or more posterior probabilities that meets or exceeds the threshold.

The data in the experience database may include data indicative of a distribution of percept values for at least one of the percepts resulting from an action that has been performed multiple times in association with a given classification or a given previously observed reference object.

The threshold may not be the same during all of the repetitions of g).

The data processing system may add data about at least one of the percepts indicated by the received test information to the experience database.

The data processing system may determine which of the percepts indicated by the received test information should have data about them added to the experience database based on the degree to which the at least one action that led to each percept caused a change in the probability that the test object has one or more of the classifications.

The data processing system may determine if the percept values of at least one percept resulting from the at least one action performed with the test object is substantially unlike the percept values of the same at least one percept resulting from the same at least one action associated with any of the classifications described in the experience database.

The data processing system may add the percept values of at least one percept resulting from the at least one action with the test object to the experience database in association with a new classification that was not in the experience database when the data processing system determines that the percept values of at least one percept resulting from at least one action performed with the test object is substantially unlike the percept values of the same at least one percept resulting from the same at least one action associated with any of the classifications described in the experience database.

The data processing system may determine at least one additional action to perform with the test object to obtain at least one percept associated with the at least one additional action and add the percept value of the at least one percept resulting from the at least one additional action to the experience database.

The initial prior probabilities may be the same.

The initial prior probabilities may be weighted based on the number of times each classification has been associated with a previously-observed reference object in the experience database.

The experience database may also contain data indicative of a time when each percept was obtained. The initial prior probabilities may be weighted based on the time each percept was obtained.

The experience database may also contain data indicative of a location where each percept was obtained. The initial prior probabilities may be weighted based on the location each percept was obtained.

The determines at least one action that should be performed may include: a) for each classification, computing a probability density function that describes a distribution of percept values expected for a percept resulting from an action that has been performed multiple times in association with the classification; b) computing a degree to which two different probability density functions for two different classifications result in similar distributions of the percept values of the same percept when performing the same action; c) multiplying the degree computed in b) by the prior probability that the test object has each classification used to compute the degree in b); d) repeating b and c for all other possible pairs of classifications; e) summing the results of all of the multiplications in c); f) repeating a-e for each of the other combinations of actions and percepts; and g) selecting the action that yields the lowest summing value in e) for any percept as the action to be performed.

The previously performed actions with the test object may be given less preference in being re-selected as the action to be performed if the previously performed action was unsuccessful in producing percept values that help discriminate between the most likely classifications.

The object test system may include at least one controllable actuator that performs the at least one action with the test object, and at least one tactile sensor that interacts with the test object and returns the test information indicative of at least one percept resulting from the at least one action.

At least one action with the test object may include sliding across a surface of the test object or contacting the test object with a varying force.

The data processing system may process the test information indicative of the at least one percept to indicate a type of surface texture on the test object, a degree of roughness or smoothness of the test object, a degree of coarseness or fineness of the test object, a degree of hardness or softness of the test object, a degree to which the test object has a springiness or dampens; and/or a thermal property of the test object.

A non-transitory, tangible, computer-readable storage medium may contain a program of instructions that cause a computer system running the program of instructions to perform one, any sub-combination, or all of the functions of the data processing system as described herein.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

FIG. 3A illustrates a side view; FIG. 3B illustrates a front view.

DETAILED DESCRIPTION OF ILLUSTRATIVE EMBODIMENTS

Figure 1:
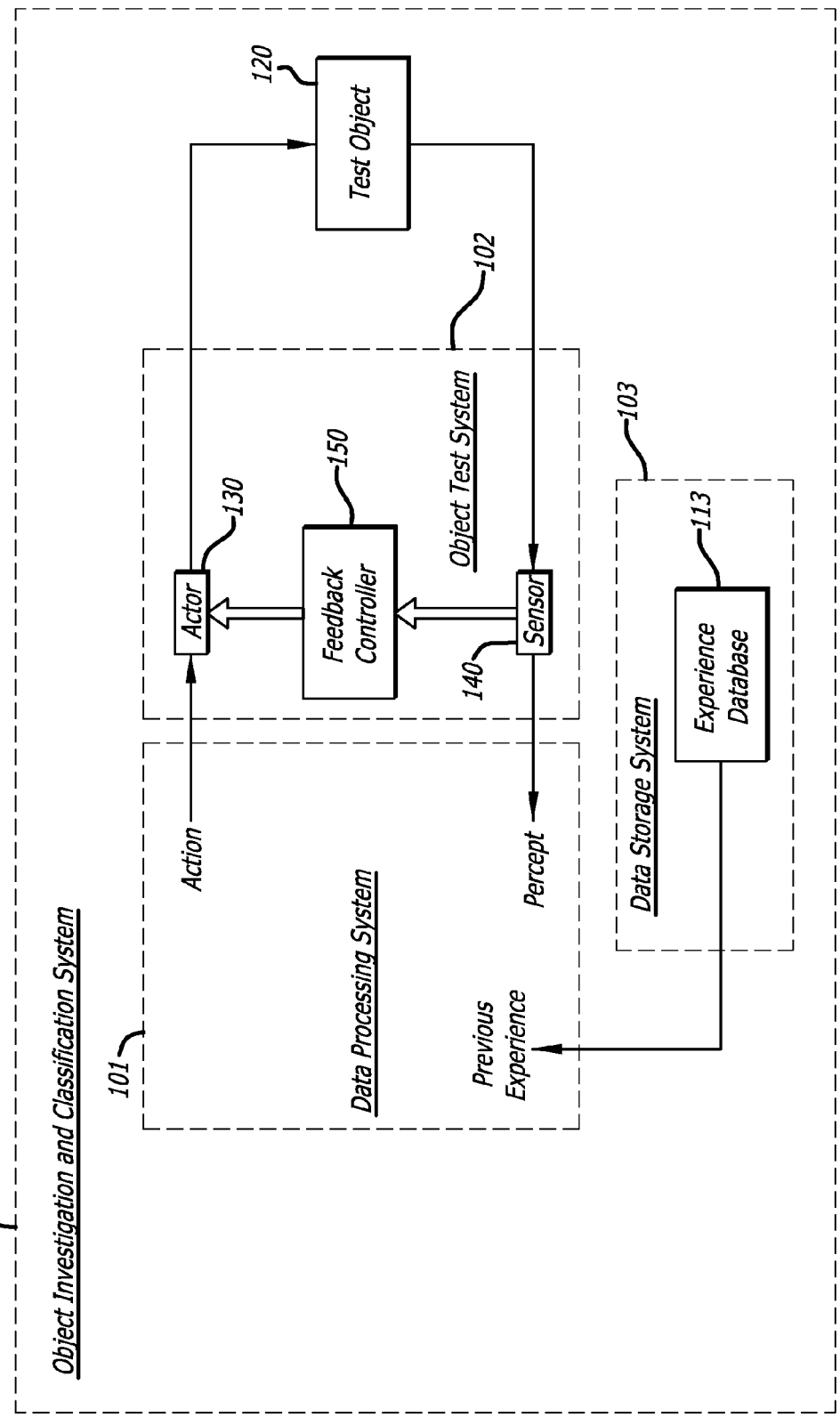
FIG. 1 illustrates an example of an object investigation and classification system that may have the ability to select and perform one or more actions with a test object, resulting in test information that may be indicative of one or more percepts that may relate to one or more classifications of the test object.

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

The following definitions apply to both this specification and the claims:

An ACTOR is a component that can interact with an OBJECT so as to cause it to generate information.

A SENSOR is a component that can detect or receive information from an OBJECT.

An OBJECT is any physical thing that is capable of interacting with one or more ACTORS and producing information that can be detected or received by one or more SENSORS.

A CLASSIFICATION is any descriptive attribute of an OBJECT.

A CLASSIFICATION SET is a grouping of two or more mutually exclusive CLASSIFICATIONS.

A PERCEPT is an abstraction of information from the one or more SENSORS when performing an ACTION that reflects a characteristic of the OBJECT.

An ACTION is a particular interaction that an ACTOR can perform with an OBJECT.

An EXPERIENCE DATABASE is a database that contains data indicative of previously executed ACTIONS with OBJECTS and PERCEPTS that result from the actions, as well as and one or more CLASSIFICATIONS of each OBJECT.

A PROBABILITY of a CLASSIFICATION of an OBJECT is a likelihood that the given OBJECT falls within the CLASSIFICATION. The PROBABILITY may be expressed in any form, such as a number between zero and one or a percentage.

A PROBABILITY DENSITY FUNCTION for a given PERCEPT and a given ACTION with a given CLASSIFICATION is the relative likelihood of the PERCEPT taking on a given value when performing the ACTION with an OBJECT that is representative of the CLASSIFICATION.

A PRIOR PROBABILITY of a CLASSIFICATION is the PROBABILITY of the CLASSIFICATION computed prior to performing an ACTION and abstracting a PERCEPT.

A POSTERIOR PROBABILITY of a CLASSIFICATION is the PROBABILITY of the CLASSIFICATION computed after performing an ACTION and abstracting a PERCEPT.

Various object investigation and classification systems for investigating and determining one or more classifications of an object are now described. An object investigation and classification system may include a physical apparatus with a tactile sensor to interact mechanically and to sense tactile information from the object in order to determine its classifications by touch. The object investigation and classification system may be capable of performing one or more actions with an object and detecting or receiving sensory information that may be computed to determine the value of one or more percepts that correlate with one or more classifications. The object investigation and classification system may have the ability to perform a large number of possible actions such that it may be impractical or time consuming for the object investigation and classification system to efficiently perform all of these actions before attempting to resolve the one or more classifications of the object. To efficiently sequence actions to perform in determining the classification(s) of an object within a single classification set consisting of mutually exclusive classifications, the object investigation and classification system may start with a set of initial prior probabilities describing the various probabilities that an object possesses each of the classifications in that classification set. The object investigation and classification system may utilize an experience database that may include records associating actions and percept values from previously-observed reference objects representative of various classifications in order to determine the optimal action that is expected to result in sensory information and consequent percept values that would be most likely to disambiguate between the most probable classification(s) of the object. The object investigation and classification system may decide to execute this optimal action once it is determined and receive sensory information that can be computed into one or more percept values. After execution of this action and computation of these percept values, the object investigation and classification system may combine the computed percept values and prior probabilities with information in the experience database to determine the posterior probabilities describing the updated probabilities that an object possesses each of the classifications in the classification set given this new information. The object investigation and classification system may iterate this process of selecting optimal queries, substituting posterior probabilities for prior probabilities until a desired confidence in a single classification within the one or more classification sets is reached.

An object may have one or more classifications corresponding with one or more classification sets. A classification may describe any descriptive attribute of the object, such as a name reflecting its identity, a category of objects which it is a part of, a feature that it possesses, or an affordance (as defined by Gibson, J. J., 1977, "The Theory of Affordances" in Perceiving, Acting, and Knowing, eds. Robert Shaw and John Bransford, ISBN 0-470-99014-7). For instance, the object may be a piece of shirt fabric with the following classifications: soft, fabric, cloth, flannel, capable of being used as a filter, 140-count twill weave double napped Canton flannel.

A classification may be applied to one or more objects. A classification set contains two or more classifications that are mutually exclusive. Classification from different classification sets may or may not overlap with, be a subset or superset of, be mutually exclusive with, or be mutually inclusive with each other across more than one previously-observed reference objects.

FIG. 1 illustrates an example of an object investigation and classification system 100 that may have the ability to select and perform one or more actions with a test object 120, resulting in test information that may be indicative of one or more percepts that may relate to one or more classifications of the test object 120. The object investigation and classification system 100 may include an object test system 102, a data storage system 103, and a data processing system 101.

Referring to FIG. 1, the object test system 102 may include one or more actors 130, one or more sensors 140, and one or more feedback controllers 150. The object investigation and classification system 100 may seek to identify one or more classifications of the test object 120 corresponding to one or more classification sets by performing actions with the test object 120 using the one or more actors 130 and computing percepts derived from information received or detected by the one or more sensors 140.

Still referring to FIG. 1, the one or more actors 130 may be mechanical actuators that can move a tactile sensor capable of measuring tactile information from a surface that it moves over. The mechanical actuators can be any component designed to physically interact with the environment, such as, but not limited to, linear stages or rotary stages and related devices familiar to those skilled in the art of mechanical systems. However, the one or more actors 130 may be any component of the object test system 102 capable of interacting with the test object 120 to cause it to generate information that can be detected by the one or more sensors 140. For example, an actor may be a computer screen capable of displaying a question to a computer user who can type in a response on a keyboard, a doctor capable of measuring a patient's temperature with a thermometer, or a motorized dolly capable of moving a video camera around a scene.

Still referring to FIG. 1, the one or more sensors 140 may be physically attached to an actuator within the one or more actors 130 to sense information about the physical interaction with the test object 120. The sensors may be capable of measuring physical properties including, but not limited to, forces, torques, vibrations, temperatures, acoustic emissions, contact position, relative velocity, acceleration, contact, humidity, magnetic flux, voltage, current, resistance, capacitance, inductance, air flow, chemical content, altitude, depth, light intensity, ultrasonic emissions, strain, proximity, video, or any other type of sensor capable of measuring physical properties which would be familiar to those skilled in the art of sensor measurements. The one or more sensors 140 may be any component of the object test system 102 capable of detecting or receiving information from the test object 120 when the test object 120 interacts with the one or more actors 130. For the examples given in the paragraph above, the one or more sensors 140 may be, respectively, a keyboard capable of detecting various keystrokes typed by a computer user when a computer screen displays a question, a thermocouple inside of a thermometer capable of producing voltages that correspond to a patient's temperature when a doctor inserts the thermometer in the patient's mouth, or a video camera capable of measuring spatial and temporal distributions of light intensity as it is moved around a scene.

Still referring to FIG. 1, the test object 120 may have a surface with tactile properties that can be sensed. The one or more sensors 140 may be tactile sensors capable of detecting tactile information from a surface when it is moved over that surface by mechanical actuators. The test object 120 may be any physical thing capable of being interacted with by the one or more actors 130 and producing information that can be sensed or detected by the one or more sensors 140. For the examples given in the paragraphs above, a test object 120 may be, respectively, a computer user capable of interpreting a question asked of them on a computer screen and typing a response on a keyboard, a patient with a temperature that can be measured by a thermometer that a doctor inserts into their mouth, or a scene that reflects light that can be detected by a video camera that is being moved by a motorized dolly.

Still referring to FIG. 1, the one or more feedback controllers 150 may include a proportional-integral-derivative controller that uses information detected by the one or more sensors 140 to control the one or more actors 130. The one or more feedback controllers 150 may also include any other type of controller designed to use feedback obtained from the one or more sensors 140 to control the one or more actors 130 using linear or non-linear methods as familiar to those skilled in the arts of feedback control of mechanical systems. For the example of a tactile sensor, the signals generated by its interaction with test object 120 may depend on the amount of force with which the one or more sensors 140 are applied to the test object 120. If the tactile sensor provides information regarding that force, then that information can be provided to the one or more feedback controllers 150 to assure that the one or more actors 130 perform the desired action with the desired force.

Still referring to FIG. 1, the data processing system 101 may be programmed to control the one or more actors 130 that may be capable of performing one or more actions to interact with the test object 120 that may be external to the object investigation and classification system 100. The one or more sensors 140 may be capable of detecting or receiving information that results from this interaction between the one or more actors 130 and the test object 120 and deliver this information to the data processing system 101 which can compute the value of one or more percepts describing the test object 120. The classification of the test object 120 may be initially unknown to the data processing system 101, which may seek to determine this classification by selecting actions to be performed by the one or more actors 130 of the object test system 102 and receiving sensory data from the one or more sensors 140 of the object test system 102.

Still referring to FIG. 1, the data processing system 101 may be programmed to select between one or more actions that the one or more actors 130 can perform with the test object 120. If the one or more actors 130 are mechanical actuators, the actions may be a predefined sequence of force, velocity or position, or any combination of these. The actions may be any particular action that the one or more actors 130 can perform with the test object 120. Referring again to the examples given in the above paragraphs, the actions may be, respectively, presenting a question to a computer user via a computer display screen, the act of measuring a patient's temperature performed by a doctor, or a particular movement made by a motorized dolly attached to a video camera.

Still referring to FIG. 1, the sensory information received by the one or more sensors 140 may be used by the data processing system 101 to compute the value of one or more of percepts that result from interactions between the one or more actors 130 and the test object 120. If the one or more sensors 140 include a tactile sensor capable of detecting tactile information from a surface when it is moved over that surface by the one or more actors 130, then the percepts may be tactile properties such as the roughness of the surface computed from the power of measured vibrations. The percepts may be any particular abstraction of signals or other information from the one or more sensors 140 that reflect a characteristic of an object. Referring again to the examples given in the above paragraphs, the percepts may be, respectively, the response computed from a sequence of keystrokes typed into a keyboard by a computer user, the temperature computed from the voltages produced by a thermocouple inside a thermometer, or an abstraction of an object shape computed from spatial and temporal distributions of light sensed by a video camera.

The object investigation and classification system 100 may be able to perform a large number of actions with its one or more actors 130 and to abstracting a large number of percepts derived from information detected or received by the one or more sensors 140 during such actions. Executing all of these actions may be too numerous, impractical, or time-consuming for the object investigation and classification system 100 to perform before identifying the one or more classifications of the test object 120. The data processing system 101 may intelligently sequence the actions to be performed by the one or more actors 130 to determine efficiently the one or more classifications of the test object 120 that the object investigation and classification system 100 seeks to identify.

Still referring to FIG. 1, the data processing system 101 may contain an experience database 113 that contains data such as records associating previously executed actions with previously computed percept values. The previously executed actions may be performed by the one or more actors 130 with previously-observed reference objects. The resulting value(s) of one or more percepts may be abstracted from signals obtained from the one or more sensors 140 during this interaction. The records of the experience database 113 may be labeled with one or more classifications from one or more classification sets for the previously-observed reference objects. The data in the experience database may also contain additional information including, but not limited to, timestamps relating to when the action was performed and other relevant environmental data such as ambient temperature, humidity, or the location of where the action was performed. The experience database 113 may also simplify these data into descriptive statistics that describe a group of the actions and/or percepts of a given classification, a given previously-observed reference object, or a given encounter with a previously-observed reference object, including, but not limited to, mean, mode, standard deviation, variance, kurtosis, skewness, standard error of the mean, number of entities observed, probability density functions, cumulative distribution functions, probability mass functions, histograms, and other descriptive statistics that are familiar to those skilled in the art of descriptive statistics.

Figure 2:
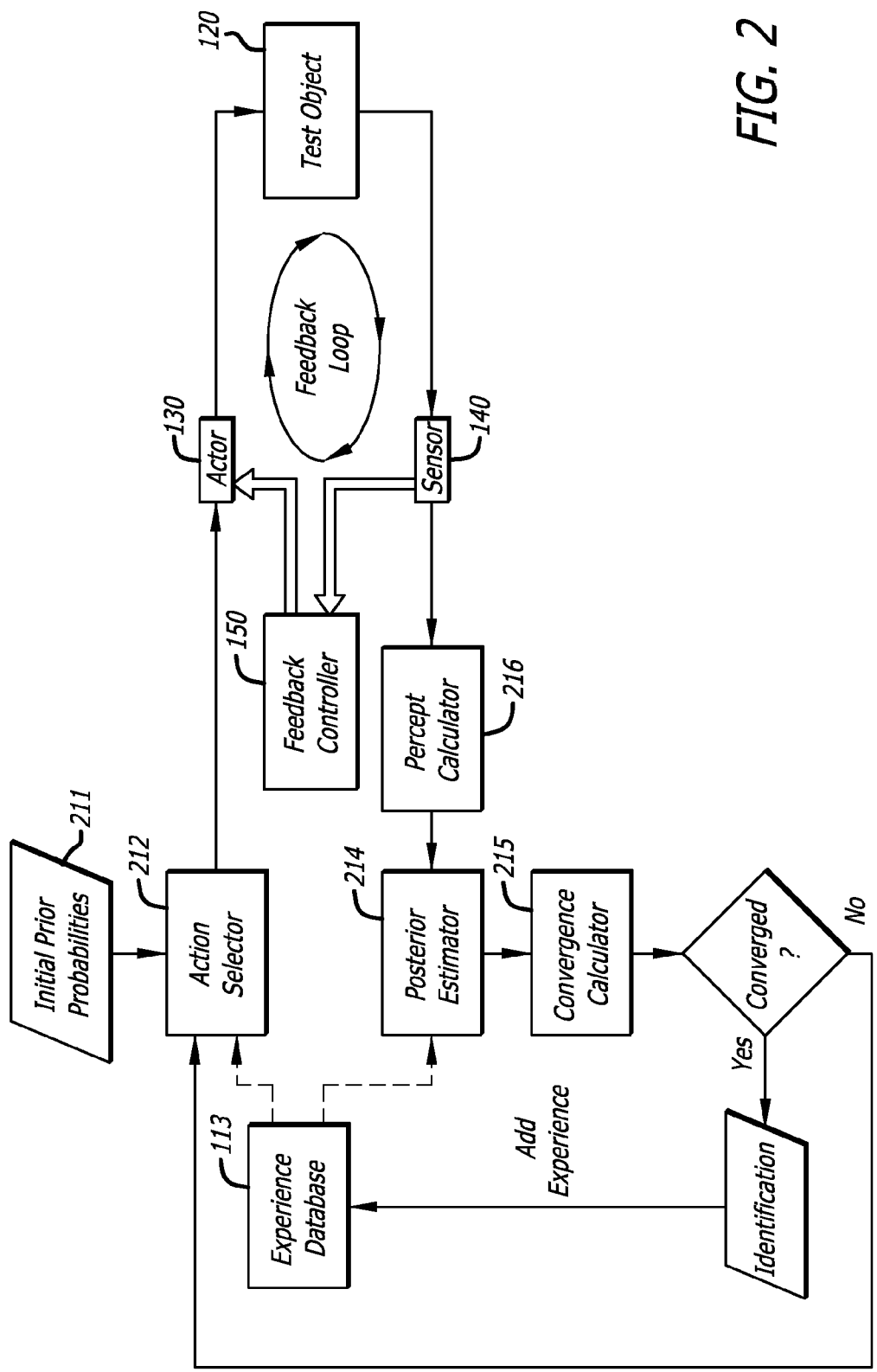
FIG. 2 illustrates an example of an algorithm that may be capable of intelligently sequencing optimal actions to perform with a test object to identify efficiently its classification.

FIG. 2 illustrates an example of an algorithm that may be capable of intelligently sequencing optimal actions to perform with the test object 120 to identify efficiently its classification. The algorithm may use initial prior probabilities 211, an action selector 212, the experience database 113, a percept calculator 216, a posterior estimator 214, a convergence calculator 215, one or more actors 130, and/or the one or more sensors 140.

Referring to FIG. 2, the algorithm may intelligently select optimal actions for the one or more actors 130 to perform with the test object 120 with an initially unknown classification in a given classification set, such that the percepts abstracted from the information detected or received by the one or more sensors 140 best disambiguates among likely classifications of the test object 120 in the given classification set, as described in more detail below.

The algorithm may be implemented by the data processing system 101.

Still referring to FIG. 2, the algorithm may start with a set of initial prior probabilities 211 that reflect the prior probabilities expected of all possible classifications within a classification set for the test object 120. The possible classifications within a classification set used in the initial prior probabilities 211 may include all of the previously encountered classifications within that classification set as stored in the experience database 113. The initial prior probabilities 211 may be computed such that they are uniformly distributed among all previously experienced object classifications for a given classification set that are stored in the experience database 113. The initial prior probabilities 211 may be computed such that they are weighted based on the relative number of times an object has been encountered with a given classification within a classification set as derived from information stored in the experience database 113. The initial prior probabilities 211 may be computed such that they are weighted based on the relative number of times an object has been encountered with a given classification within a classification set over a specified period of time as derived from data stored in the experience database 113. The initial prior probabilities 211 may be computed such that they are weighted based on the number of times and recency an object has been encountered with a given classification within a classification as derived from information stored in the experience database 113. The initial prior probabilities 211 may be computed such that they are weighted based on the relative number of times an object has been encountered with a given classification within a classification set in the current location that the object investigation and classification system 100 is exploring the test object 120 as derived from information stored in the experience database. The initial prior probabilities 211 may alternatively be set by an external system and may be based on information for which the object investigation and classification system 100 may have no available sensors.

Still referring to FIG. 2, the initial prior probabilities 211 may be passed to the action selector 212. The action selector may utilize information in the experience database 113 to determine which action to be performed by the one or more actors 130 is anticipated to yield a percept value that is most likely to disambiguate among the most likely classifications of the test object 120, as described by the initial prior probabilities 211. To accomplish this, the action selector 212 may utilize data in the experience database 113 to estimate a probability density function that reflects the relative likelihood of obtaining a percept value when performing a given action with the test object 120, if that test object 120 were to have a given classification. The probability density function for a given percept when performing a given action on an object with a given classification may be assumed to have a normal distribution, binomial distribution, uniform distribution over a specified range, Cauchy distribution, chi-square distribution, F distribution, t distribution, lognormal distribution, exponential distribution, gamma distribution, binomial distribution, Poisson distribution, bimodal distribution, or any other distribution as familiar to those skilled in the art of probability distributions. The information in the experience database 113 may be used to determine a suitable probability density function as familiar to those skilled in the art of curve fitting. The probability density function for a given percept when performing a given action with the test object 120 with a given classification can be computed using data in the experience database of previous values of the percept obtained when performing the given action on all previously-observed reference objects known to be members of the given classification. For instance, if the distribution is assumed to be normal, the probability density function can be computed based on the mean and standard deviation of said previous values using methods familiar to those skilled in the art of probability distributions. The probability density function may also be computed based on normalized histograms representative of actual data contained within the experience database 113. The information used in the experience database 113 to compute the probability distribution may be all records of the specified percept obtained when performing the given action on all previously-observed reference objects with the given classification. The information used in the experience database 113 to compute this probability distribution may give preferential weighting to records that have occurred over a specified period of time, have occurred recently, have occurred in a specified location, or some other subset of records of the specified percept obtained when performing the given action on all previously-observed reference objects with the given classification. Once the probability density functions have been computed for each possible combination of actions, percepts and classifications, the action selector 212 may further compute the degree of overlap between two probability density functions derived from two different pairs of mutually exclusive classifications within a classification set for a given percept and action. The degree of overlap between these two probability density functions could be computed by analyzing the intersecting regions of the two probability density functions, multiplying the two probability density functions, multiplying then taking the square root of the two probability density functions, or any other method to determine the amount of overlap between two different probability density functions familiar to those skilled in the art of probability distributions. The degree of overlap between any two classifications within a classification set may be weighted by the prior probabilities of both classifications to determine the anticipated ambiguity of a percept between two classifications. The resulting terms could be summed across all possible pairings of classifications within a classification set for a given percept and a given action to determine the total anticipated ambiguity for that given percept and that given action. The action selector 212 could then select the action to perform and one or more of the resulting percepts to abstract based on the action and percepts that have the lowest value of total anticipated ambiguity. An exemplary set of equations for performing this computation for probability density functions that are normally distributed is provided in the box below.

Referring to the box below, $a_i$ is a given action, $p_j$ is a given percept that can be computed from sensory information obtained from performing the action $a_i$, $c_m$ is a given classification, $\bar{x}_{a_i,p_j,c_m}$ is the mean value of percept $p_j$ obtained when performing action $a_i$ on all previously-observed reference objects in the experience database with the classification $c_m$, $\sigma_{a_i,p_j,c_m}$ is the standard deviation of percept $p_j$ obtained when performing action $a_i$ on all previously-observed reference objects in the experience database 113 with the classification $c_m$, $PDF_{a_i,p_j,c_m}(x)$ is the probability density function that reflects the relative likelihood of obtaining percept value x for percept $p_j$ when performing action $a_i$ on objects with classification $c_m$ based on previously-observed reference objects in the experience database 113, $DO_{a_i,p_j,c_{m,n}}$ is the degree of overlap for percept $p_j$ between classification $c_m$ and classification $c_n$ when performing action $a_i$ based on previously-observed reference objects in the experience database 113, $P(c_m)$ and $P(c_n)$ are the respective prior probabilities of classification $c_m$ and classification $c_n$, $AA_{a_i,p_j,c_{m,n}}$ is the anticipated ambiguity of percept $p_j$ between classification $c_m$ and classification $c_n$ when performing action $a_i$ based on previously-observed reference objects in the experience database 113 and the prior probabilities $P(c_m)$ and $P(c_n)$, $TAA_{a_i,p_j}$ is the total anticipated ambiguity of percept $p_j$ when performing action $a_i$ based on previously-observed reference objects in the experience database 113 and the prior probabilities, OAP is the optimal action and percept to best disambiguate between the most likely prior probabilities based on previously-observed reference objects in the experience database 113 and the prior probabilities.

$$\text{given mean } (\bar{x}_{a_i,p_j,c_m}) \text{ and st dev } (\sigma_{a_i,p_j,c_m}) \qquad 1)$$

$$\text{compute probability density function} \qquad 2)$$

$$PDF_{a_i,p_j,c_m}(x) \propto \frac{1}{\sqrt{2\pi\sigma^2_{a_i,p_j,c_m}}} e^{-\frac{(x-\bar{x}_{a_i,p_j,c_m})^2}{2\sigma_{a_i,p_j,c_m}}}$$

$$\text{compute degree of overlap} \qquad 3)$$

$$DO_{a_i,p_j,c_{m,n}} = \sqrt{PDF_{a_i,p_j,c_m} \cdot PDF_{a_i,p_j,c_n}}$$

$$\text{given prior probability } P(c_m) \text{ for all } m \qquad 4)$$

$$\text{compute anticipated ambiguity} \qquad 5)$$

$$AA_{a_i,p_j,c_{m,n}} = DO_{a_i,p_j,c_{m,n}} P(c_m) P(c_n)$$

$$\text{compute total anticipated ambiguity} \qquad 6)$$

$$TAA_{a_i,p_j} = \sum_m \sum_n AA_{a_i,p_j,c_{m,n}}$$

$$\text{determine optimal action and percept} \qquad 7)$$

$$OAP = \min(TAA_{a_i,p_j})$$

Still referring to FIG. 2, the one or more actors 130 may perform the action selected by the action selector 212 with the test object 120. The one or more sensors 140 may detect or receive information from the test object 120 when performing this action and pass this information on to the percept calculator 216 that may compute one or more percept values that describe a property of the test object 120, specific examples are provided below. The one or more sensors 140 may also deliver detected or received information to the one or more feedback controllers 150 to control the one or more actors 130 as described above.

Still referring to FIG. 2, the percept calculator 216 may pass the one or more calculated percept values on to the posterior estimator 214, which may use this information to compute the posterior probabilities that the test object 120 may be of a given classification in a classification set. The posterior estimator 214 may use statistical inference techniques to compute the posterior probabilities using the one or more computed percept values from the percept calculator 216, probability density functions that describe the relative likelihood of obtaining each value of a percept when performing a given action with an object that is representative of a given classification in a classification set as computed above, and prior probabilities, using methods such as, but not limited to, Bayesian inference or other statistical inference techniques as familiar to those skilled in the art of statistical inference.

Still referring to FIG. 2, the posterior probabilities computed by the posterior estimator 214 may be analyzed by the convergence calculator 215 to determine if any classification within a classification set has reached a probability that exceeds a given threshold. If this threshold has not been met, the process can be iterated by substituting the computed posterior probabilities from the posterior estimator 214 into the prior probabilities used to compute the optimal action by the action selector 212 and repeating the above sequence until the convergence calculator 215 has determined that at least one classification within a classification set has reached a probability that meets or exceeds a given threshold. If only one classification within a classification set has reached a probability that meets or exceeds a given threshold, that classification may be selected as the classification of the test object 120. If more than one classification within a classification set has reached a probability that meets or exceeds a given threshold, the classification with the highest threshold may be selected as the classification of the test object 120. Alternatively, if more than one classification within a classification set has reached a probability that meets or exceeds a given threshold, the classifications may be selected as the multiple satisfactory classifications of the object. The threshold used by the convergence calculator 215 may be a fixed value through all iterations, or it may change between iterations, including, but not limited to starting out initially high in the first iteration, but decreasing as more iterations are performed to avoid both quickly making an incorrect conclusion or indefinitely performing a large number of actions without ever meeting this threshold.

Still referring to FIG. 2, after the convergence calculator 215 has determined the classification of the test object 120, the one or more actions conducted by the one or more actors 130 and the associated percept values computed by the percept calculator 216 may be added to the experience database 113 along with the classification of the test object 120, as determined by the convergence calculator 215. The data processing system 101 may add all of the actions and resulting percept values obtained through this experience to the experience database 113, or only those that were found to be useful in identifying the classification that was selected. The actions and percepts to be labeled useful in identifying the classification that was selected may be found by analyzing the change between the prior probability and the posterior probability of the classification that was selected, as calculated by the posterior estimator 214. A combination of an action and percept that resulted in a substantial change between the prior probability and the posterior probability in the classification that was selected may be labeled useful. A substantial change may be defined as an increase meeting or exceeding a predetermined threshold, or an increase or decrease meeting or exceeding a predetermined threshold. This process may enable the experience database 113 to contain greater amounts of data for actions and percepts that have proven to be useful in determining the classification of an object, enabling it to perform more efficiently in future classifications of objects.

The above algorithm describes a method that may be capable of intelligently sequencing actions to identify efficiently a single classification within a classification set. Various approaches may be taken to solve for two or more classifications within two or more corresponding classification sets. One approach may be to set the initial prior probabilities 211 for the two or more classifications within the two or more classification sets, then use the above described algorithm to select the optimal actions to identify the classification within the first classification set while also using the posterior estimator 214 to update the probabilities of the other classifications within the other classification sets with these selected actions and resulting percept values. Upon converging on a classification within the first classification set, the process may be repeated for the remaining classifications to be identified in the remaining classification sets. Another variation to the approach above may be to select the optimal action to identify the classification within the classification set that has the highest probability that has yet to exceed the threshold across all possible classifications across all classification sets seeking to be identified. Another approach may be to converge the two or more classification sets into a single classification set by combining all possible combinations of each classification between all classification sets seeking to be identified. For instance, if one classification set contained the three mutually exclusive colors red, green and blue and another classification set contained the two mutually exclusive shapes circle and square, the new classification set would contain 6 mutually exclusive merged classifications: red-circle, red-square, green-circle, green-square, blue-circle, and blue-square. This merged set may be treated as a single classification set; however, depending on the relationships between classifications within the classification sets, some of these combined classifications may be mutually exclusive. Instead, the new classification set may consist of all observed instances of possible combinations of each classification between all classification sets seeking to be identified.

The algorithm for investigating and determining the classification of an object that may be implemented by the data processing system 101 may benefit from an experience database 113 that contains a large amount of previous experience describing the values of one or more percepts that arise from actions that are useful for disambiguating possible classifications within a classification set. Because the useful actions and percepts for disambiguating possible classifications within a classification set may not be known prior to collecting this previous experience, the object investigation and classification system 100 could be initially programmed to perform a small number of repetitions over many possible candidate actions with the test object 120 and compute values of one or more percepts for each candidate action to be stored in the experience database 113 to gain an initial set of information describing previously-observed reference objects. Through executing the above-described algorithm in future encounters and adding experiences of actions and percepts determined to be useful in disambiguating possible classifications of a test object 120 within a classification set, the experience database 113 may automatically acquire a larger amount of experience in a smaller set of actions and percepts found to be useful.

Estimating probability density functions of a given percept for a given action for a given classification from a limited amount of information in the experience database 113 may result in errors between the estimated probability density function and the true probability density function of that percept for a given action and given classification. If the previous experience in the experience database 113 is limited, these errors may become more severe when the posterior estimator 214 attempts to compute the posterior probabilities based on more than one percept at a time. This phenomenon is known as the curse of dimensionality (Jain, A K, R P W Duin, and J. Mao. 2000. "Statistical Pattern Recognition: a Review." IEEE Transactions on Pattern Analysis and Machine Intelligence 22 (1): 4-37.) and is familiar to those skilled in the arts of statistical pattern recognition. To circumvent this, the posterior estimator 214 may initially analyze only a single percept for a given action when computing posterior probabilities, considering only the optimal percept as determined by the action selector 212, and then gradually increase the number of percepts to contribute to the computation of the posterior probabilities by the posterior estimator 214 as more experience is obtained in the experience database 113. All percepts obtained when conducting an action, including those that may not be used by the above algorithm, may still be added to the experience database 113 after a classification is identified by the convergence calculator 215.

The total anticipated ambiguity for a given percept and a given action as computed by the action selector 212 could consider the number of times the given action and resulting percept has been performed on the test object 120 that the object investigation and classification system 100 is currently investigating and use this information to provide a more accurate prediction of the total anticipated ambiguity. For instance, if the action selector 212 suggests a particular action and percept to be optimal based on information contained in the experience database 113 and current prior probabilities, yet the object investigation and classification system 100 has previously performed this action and computed a value for this percept on the test object 120 that it is currently investigating without yielding useful information to disambiguate likely classifications of the object, this information may indicate that the total anticipated ambiguity as computed by the action selector should be higher. To accomplish this the total anticipated ambiguity as computed by the action selector could include a penalty factor based on the number of times the given action has been repeated, such as, but not limited to, raising the total anticipated ambiguity to a power that becomes greater than one according to the number of times this has occurred without producing significant changes in the posterior probabilities. This may serve to encourage the action selector 212 to select new actions if the selected actions are not helping the object investigation and classification system 100 converge on a given classification.

To avoid the need for supervised learning to label classifications, the data processing system 101 may be programmed create new classifications based on the distributions of actions and percepts in the experience database 113. The data processing system 101 may be programmed to use cluster analysis to identify if the distribution of percepts computed while performing actions with a test object 120 are likely to correspond to previously-experienced objects of one or more existing classifications or if they are more likely to represent one or more novel classifications. If the latter, then the data processing system 101 may add one or more new classifications to the experience database 113, with each such new classification containing the previously experienced actions and percepts (or a statistical summary thereof) that are most closely associated with the new one or more classifications using methods familiar to those skilled in the art of cluster analysis and unsupervised learning. Prior to or after adding the one or more new classifications to the experience database 113, the data processing system 101 may also perform one or more additional actions and obtain one or more percepts resulting from each action and add this information to the experience database 113 to obtain additional information on the new classification.

A prior probability or a posterior probability for a given classification may be a number between zero and one corresponding to the likelihood that the test object 120 possesses the given classification or it may be any other value on any scale that correlates with the likelihood that the test object 120 possesses the given classification.

Figure 3A:
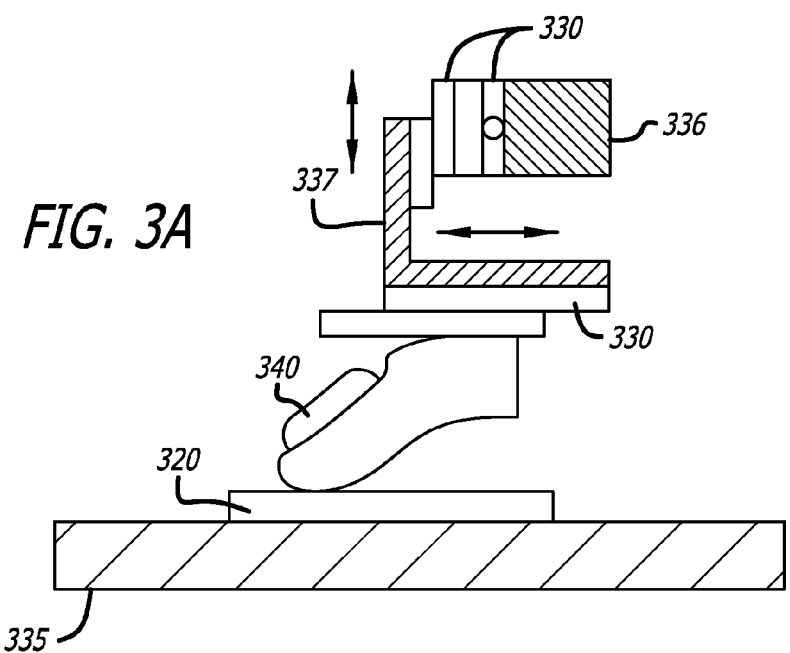
FIG. 3A-3B illustrates an example of the object test system illustrated in FIG. 1 that can explore tactile properties of a flat tactile surface.
Figure 3B:
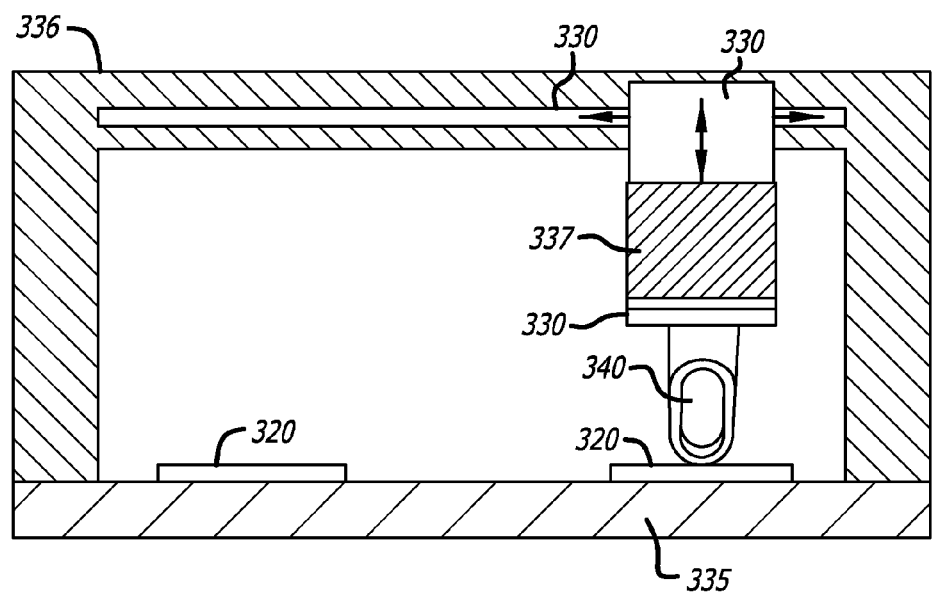

FIG. 3A-3B illustrates an example of the object test system 102 illustrated in FIG. 1 that can explore tactile properties of a test object, such as a flat tactile surface 320. The object test system 102 may include a base 335, a gantry 336, a mechanical adapter 337, one or more linear actuators 330, and a tactile sensor 340. FIG. 3A is a side view. FIG. 3B is a front view.

The one or more linear actuators 330 may be capable of moving the tactile sensor 340 to perform actions that are similar to the movements humans make when exploring objects by touch. The tactile sensor 340 may have sensory capabilities, sensitivity, resolution, and mechanical properties and may interact with objects being explored in ways that are similar to those of human fingertips. The one or more feedback controllers 150 may make use of information from the tactile sensor 340 or from multiple tactile sensors instrumented on the one or more linear actuators 330 to control exploratory movement. Signal processing algorithms may measure percepts that correspond to the linguistic descriptions of percepts observed by humans when identifying tactile properties of objects. The experience database 113 may be used and may include previous experience exploring similar objects and may include and associate descriptors of each exploratory movement with linguistic measurements of object properties. A biologically inspired decision making process may be employed for determining an optimal next exploratory movement to make. The object test system 102 may apply these tactile exploration, measurement and perception technologies in quality control, product design, and in other fields.

Still referring to FIG. 3A, the gantry 336 may be attached to the base 335 to hold the one or more linear actuators 330. The one or more linear actuators 330 may be coupled together with the mechanical adapter 337 that position the tactile sensor 340 over the tactile surface 320. The gantry 336, base 335, and the mechanical adapter 337 may be made of any engineering materials suitable as structural materials, including, but not limited to, metals, plastics, ceramics, or any other materials familiar to those skilled in the art of engineering design. The base 335 may have a high mass to dampen vibrations from external sources. The one or more linear actuators 330 may be any type of device capable of creating movement, such as movement in a straight line, such as hydraulic actuators, pneumatic actuators, piezoelectric actuators, electro-mechanical actuators, or any other type of actuator capable of creating motion in a straight line as familiar to those skilled in the art of actuation. The one or more linear actuators 330 may be programmed to move the tactile sensor 340 over the tactile surface 320 with a movement profile that resembles the types of exploratory movements humans typically make. These exploratory movements may be similar to the movements humans make when exploring objects by touch and may include, but are not limited to, pressing the tactile sensor 340 into the tactile surface 320 with a predetermined profile of force, velocity, displacement, or combination of force, velocity, and displacement; or sliding the tactile sensor 340 over the tactile surface 320 with a predetermined trajectory of velocities in one or more directions. Any of the above movements may use sensory data from the tactile sensor 340 to control force, displacement or velocity as described below.

The tactile sensor 340 may have sensory capabilities, sensitivity, resolution, and mechanical properties and may interact with objects being explored similar to those of a human fingertip. The tactile sensor 340 may be the BioTac (made by SynTouch LLC, Los Angeles, Calif.). The ability of the tactile sensor 340 to produce interactions between the tactile surface 320 that are similar to those that would be produced when interacting with a human fingertip may benefit from the tactile sensor 340 having similar mechanical properties as the human fingertip, such as similar compliance, shape, and size. The tactile sensor 340 may also or instead have similar features as the human fingertip, such as a fingernail that facilitates the transduction of shear forces applied to the fingerpad, and fingerprints that enhance vibrations sensed when sliding the tactile sensor 340 over a textured surface. The ability of the tactile sensor 340 to perceive sensations similar to those a human may perceive when exploring the tactile surface 320 may benefit from the tactile sensor 340 having sensory modalities similar to those found in human skin, such as sensitivity to contact location, normal and shear forces, vibrations, and/or temperature.

The one or more feedback controllers 150 that make use of information from the tactile sensor 340 or sensors instrumented on the one or more linear actuators 330 to control exploratory movements may include the ability to control the specified force of the one or more linear actuators 330 in the normal axis. The specified force in the one or more linear actuators 330 in the normal axis may be controlled using the one or more feedback controllers 150 that may make use of sensory information from the tactile sensor 340 or other sensors instrumented on the one or more linear actuators 330 in the normal axis, such as force plates, motor current sensors, strain gages, or other technologies familiar to those skilled in the art of force measurement. The tactile sensor 340 may be a fluid-filled tactile sensor capable of sensing fluid pressure. The fluid pressure in the tactile sensor 340 may be used to stabilize contact force by adjusting the position of the one or more linear actuators 330 in the normal axis by means of a feedback controller that maintains the fluid pressure reading at a constant value.

The signal processing strategies for the measurement of percepts that correspond to the linguistic descriptions of percepts observed by humans when identifying tactile properties of objects may be computed from the sensory information obtained from the tactile sensor 340 and/or from other sensors contained in the one or more linear actuators 330, such as position encoders, strain gages, motor current sensors, force plates, or other technologies familiar to those skilled in the art of actuation. Examples of linguistic descriptions of percepts observed by humans have been observed in prior art and may include, but are not limited to: properties relating to surface texture including, but not limited, to roughness, coarseness, slipperiness, or regularity; properties relating to compliance, including, but not limited to, hardness or springiness; and/or properties relating to thermal properties, including, but not limited to thermal effusivity, thermal conductivity, and heat capacity. The percept of texture roughness may be computed by analyzing the logarithm of the variance of vibrations measured by the tactile sensor 340 when sliding over a surface. The percept of texture coarseness can be computed by transforming the vibrations measured by the tactile sensor 340 into the frequency domain with a fast Fourier transform and multiplying the power of the individual frequency bins by their respective frequency and summing all respective terms, then dividing the result by the total power of all frequency bins, and taking the logarithm of the result. The percept of texture slipperiness can be computed from the inverse of the tangential load of the actuator when sliding at a specified contact force. The percept of texture regularity can be computed from the diffusivity of the spectral content in the Fourier transform when the tactile sensor 340 slides over a tactile surface. The percept of hardness can be computed as the inverse of mechanical compliance, which may be determined by measuring the displacement of the tactile sensor 340 as the force between the tactile sensor 340 and the test object 120 is changed by the one or more linear actuators 330. The percept of thermal effusivity can be computed from the measurement of temperature over time in the tactile sensor 340 that is heated above ambient temperature. Other signal processing strategies, such as those described in (Lin, C H, T W Erickson, J A Fishel, undefined author, N Wettels, and G E Loeb. 2009. "Signal Processing and Fabrication of a Biomimetic Tactile Sensor Array with Thermal, Force and Microvibration Modalities." In Proc. IEEE International Conference on Robotics and Biomimetics, 129-134.; Su, Z, J A Fishel, T Yamamoto, and G E Loeb. 2012. "Use of Tactile Feedback to Control Exploratory Movements to Characterize Object Compliance." Frontiers in Neurorobotics 6(7): 1-12.; Fishel, J A, and G E Loeb. 2012. "Bayesian Exploration for Intelligent Identification of Textures." Frontiers in Neurorobotics 6(4): 1-20.; Chu, V, I McMahon, L Riano, C G McDonald, Q He, J M Perez-Tejada, M Arrigo, et al. 2013. "Using Robotic Exploratory Procedures to Learn the Meaning of Haptic Adjectives." In Proc. IEEE International Conference on Robotics and Automation.) for characterizing tactile properties of texture, compliance and thermal properties may also be used.

The one or more linear actuators 330 may be precision components designed to produce smooth motions with high accuracy and repeatability with low mechanical vibration such that the variability and noise of the one or more linear actuators 330 produce variability of percept values that is similar to those that would be computed if the linear actuators were not moving. Such precision components may include, but are not limited to, actuators with precision cross roller bearings, actuators with air bearings, actuators with hydraulic cylinders and other actuators and mechanical linkages familiar to those skilled in the art of mechatronic design. The fidelity of sensor information collected from the tactile sensor 340 may benefit from the low background noise levels produced from such precision components as discussed below. An example of a suitable linear actuator may include the ANT95-75-L (Aerotech, Pittsburg, Pa.) or other similar product families. The apparatus may have two linear actuators 330, one to control the movement in the direction normal to the tactile surface 320 and another to control the movement in the direction tangential to the tactile surface 320. However, the actuators need not be linear and alternative technologies such as rotary actuators may be used as familiar to those skilled in the art of mechatronic design.

The above described object investigation and classification system 100 incorporating the tactile sensor 340 and linear actuators 330 was used in an experiment to test its ability to identify a single texture within a set of 117 different textures. (Fishel, J A, and G E Loeb. 2012. "Bayesian Exploration for Intelligent Identification of Textures." Frontiers in Neurorobotics 6(4): 1-20.). The data processing system 101 was programmed to control the one or more linear actuators 330 to produce three different actions that consisted of sliding motions at different contact forces and velocities (0.20N contact force, 6.31 cm/s sliding velocity; 0.5N contact force, 2.51 cm/s sliding velocity; and 1.26N contact force, 1 cm/s sliding velocity). The data processing system 101 was programmed to receive test information from the tactile sensor 340 and additional sensors within the one or more linear actuators 330 and to compute the following three percepts from each action: i) the percept of texture roughness, which was computed by analyzing the logarithm of the variance of vibrations measured by the tactile sensor 340 when sliding over a surface; ii) the percept of texture coarseness, which was computed by transforming the vibrations measured by the tactile sensor 340 into the frequency domain with a fast Fourier transform and multiplying the power of the individual frequency bins by their respective frequency and summing all respective terms, then dividing the result by the total power of all frequency bins, and taking the logarithm of the result; and iii) the percept of texture slipperiness, which was computed from the inverse of the tangential load on the actuator when sliding at the specified contact force. Using the algorithm described above, the object investigation and classification system 100 obtained 95.4% accuracy over 117 textures, 99.6% accuracy discriminating between pairs of nearly identical textures (in comparison, human subjects were only able to obtain 81.3% performance in discriminating these pairs of nearly identical textures), and 100% performance over 10 textures intentionally selected due to their dissimilarity. In comparison, other methods were found to have only marginal performance accuracies when using a small number of highly distinctive surfaces that would be trivial to discriminate for a human observer or for the object investigation and classification system 100. Examples of classification performance in previous literature include: 62% over 10 textures (de Boissieu, F, C Godin, B Guilhamat, D David, C Serviere, and D Baudois. 2009. "Tactile Texture Recognition with a 3-Axial Force MEMS Integrated Artificial Finger." In Proc. Robotics: Science and Systems, 49-56.), 89.9-94.6% over 10 textures (Giguere, P, and G Dudek. 2011. "A Simple Tactile Probe for Surface Identification by Mobile Robots." IEEE Transactions on Robotics 27 (3): 534-544.), 95% over 20 textures (Sinapov, J, V Sukhoy, R Sahai, and A Stoytchev. 2011. "Vibrotactile Recognition and Categorization of Surfaces by a Humanoid Robot." IEEE Transactions on Robotics 27 (3): 488-497.), 97.6% over 3 textures (Oddo, C M, M Controzzi, L Beccai, C Cipriani, and M C Carrozza. 2011. "Roughness Encoding for Discrimination of Surfaces in Artificial Active-Touch." IEEE Transactions on Robotics 27 (3): 522-533.), and 95% over 8 textures (Jamali, N, and C Sammut. 2011. "Majority Voting: Material Classification by Tactile Sensing Using Surface Texture." IEEE Transactions on Robotics 27 (3): 508-521.).

These tactile exploration, measurement, and perception technologies may be used in quality control and product design and in other fields. The above described system that seeks to mimic biological processes for identifying the classification of an object based on its tactile properties may be used to provide quantitative measures of human tactile perception. The object investigation and classification system 100 may be used in product development applications to determine if one product has a similar feel to another product. In order to determine the attribute of a particular feel, the object investigation and classification system 100 may acquire an experience database that is organized according to classifications reflecting various possible feels. Such an experience database may be accumulated by performing various actions and recording the resulting percept values obtained with reference objects already classified according to the various possible feels by humans who may have experience in making such classifications. Design and manufacturing industries for garments, paper goods, consumer electronics, cosmetics, skin and hair care products, prepared foods, and other products commonly employ humans with expertise in classifying objects and materials according to feel. Classification according to feel may be useful when designing a product that seeks to mimic the feel of another product, or restore the feel of an object that has been damaged using various surface treatments. The above described object investigation and classification system 100 may also be useful for determining which combinations of classifications have desirable or undesirable traits that can be identified in consumer preference studies. The above described system may also be useful in applications of quality control.

Referring to FIG. 3B, an additional linear actuator 330 may run along the length of the gantry 336. This actuator may permit a single tactile sensor to be repositioned to explore multiple tactile surfaces. The ability to rapidly change between multiple tactile surfaces may improve the output of classification system 100 when characterizing a large number of objects. This may also benefit from the use of guides to assist the operator with the placement and orientation of the surface in the exploratory range of the machine which may be, but not limited to, laser-generated guides or other indexing tools as familiar to those skilled in the art of industrial equipment design. The ability to change rapidly between multiple tactile surfaces may facilitate comparison between a standardized tactile surface 320 that remains in place as a reference.

Figure 4:
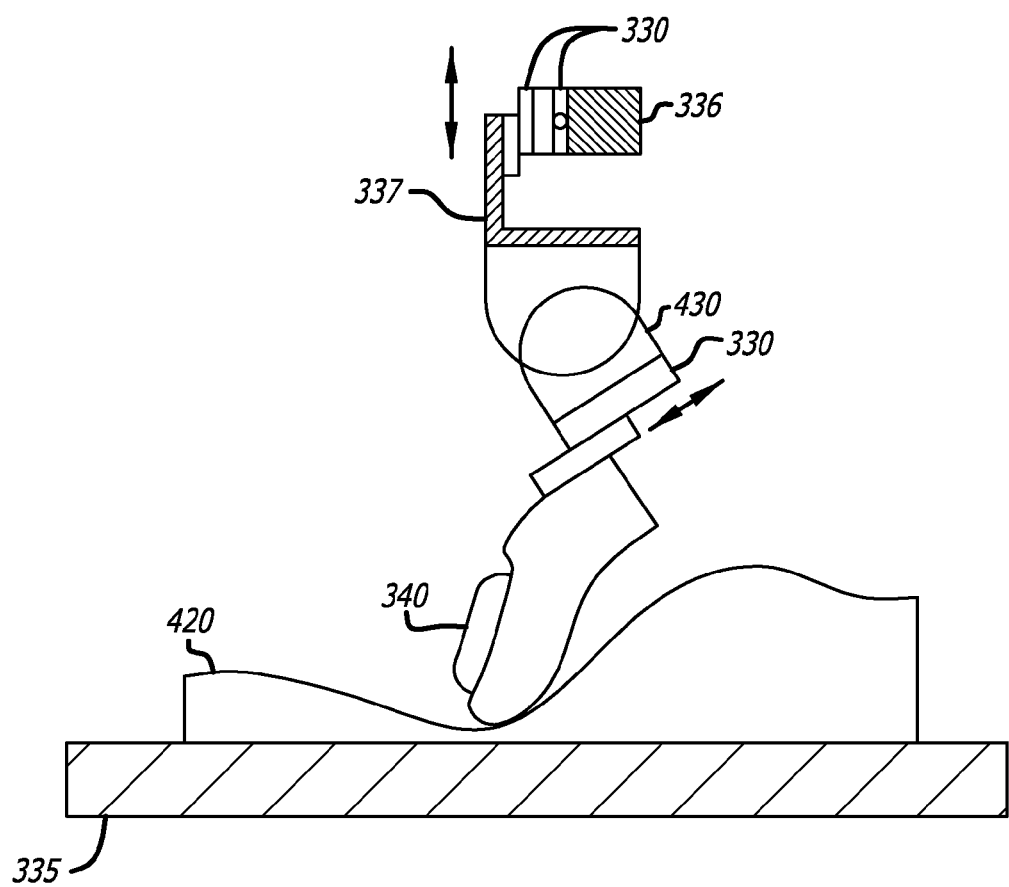
FIG. 4 illustrates an example of the object test system illustrated in FIG. 1 that can explore tactile properties of a contoured tactile surface.

FIG. 4 illustrates an example of an object test system that can explore tactile properties of a contoured tactile surface 420. The object test system may have the base 335, the gantry 336, the one or more linear actuators 330, one or more rotary actuators 430, and the tactile sensor 340.

Referring to FIG. 4, the one or more rotary actuators 430 may be used to align the tactile sensor 340 so that it is normal to the contoured tactile surface 420. Information from four electrodes in the tip of a BioTac, for example, may be delivered to the one or more feedback controllers 150 to control the orientation of the BioTac with respect to the contoured tactile surface 420, as described by (Su, Z, J A Fishel, T Yamamoto, and G E Loeb. 2012. "Use of Tactile Feedback to Control Exploratory Movements to Characterize Object Compliance." Frontiers in Neurorobotics 6(7): 1-12.).

Unless otherwise indicated, the data processing system 101, the object test system 102, and the data storage system 103 may each be implemented with the same or a different computer system configured to perform the functions that have been described herein for the component. Each computer system may include one or more processors, tangible memories (e.g., random access memories (RAMs), read-only memories (ROMs), and/or programmable read only memories (PROMS)), tangible storage devices (e.g., hard disk drives, CD/DVD drives, and/or flash memories), system buses, video processing components, network communication components, input/output ports, and/or user interface devices (e.g., keyboards, pointing devices, displays, microphones, sound reproduction systems, and/or touch screens).

Each computer system may include one or more computers at the same or different locations. When at different locations, the computers may be configured to communicate with one another through a wired and/or wireless network communication system.

Each computer system may include software (e.g., one or more operating systems, device drivers, application programs, and/or communication programs). When software is included, the software includes programming instructions and may include associated data and libraries. When included, the programming instructions are configured to implement one or more algorithms that implement one or more of the functions of the computer system, as recited herein. The description of each function that is performed by each computer system also constitutes a description of the algorithm(s) that performs that function.

The software may be stored on or in one or more non-transitory, tangible storage devices, such as one or more hard disk drives, CDs, DVDs, and/or flash memories. The software may be in source code and/or object code format. Associated data may be stored in any type of volatile and/or non-volatile memory. The software may be loaded into a non-transitory memory and executed by one or more processors.

The components, steps, features, objects, benefits, and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits, and advantages. These also include embodiments in which the components and/or steps are arranged and/or ordered differently.

For example, the data processing system 101 and the data storage system 103 may be combined into a single component such as a microcomputer. For example, the one or more feedback controllers 150 may be part of the object test system 102 or part of the data processing system 101.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases from a claim means that the claim is not intended to and should not be interpreted to be limited to these corresponding structures, materials, or acts, or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows, except where specific meanings have been set forth, and to encompass all structural and functional equivalents.

Relational terms such as "first" and "second" and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element preceded by an "a" or an "an" does not, without further constraints, preclude the existence of additional elements of the identical type.

None of the claims are intended to embrace subject matter that fails to satisfy the requirement of Sections 101, 102, or 103 of the Patent Act, nor should they be interpreted in such a way. Any unintended coverage of such subject matter is hereby disclaimed. Except as just stated in this paragraph, nothing that has been stated or illustrated is intended or should be interpreted to cause a dedication of any component, step, feature, object, benefit, advantage, or equivalent to the public, regardless of whether it is or is not recited in the claims.

The abstract is provided to help the reader quickly ascertain the nature of the technical disclosure. It is submitted with the understanding that it will not be used to interpret or limit the scope or meaning of the claims. In addition, various features in the foregoing detailed description are grouped together in various embodiments to streamline the disclosure. This method of disclosure should not be interpreted as requiring claimed embodiments to require more features than are expressly recited in each claim. Rather, as the following claims reflect, inventive subject matter lies in less than all features of a single disclosed embodiment. Thus, the following claims are hereby incorporated into the detailed description, with each claim standing on its own as separately claimed subject matter.

The invention claimed is:

1. An object investigation and classification system comprising:
   an object test system that includes one or more actors and sensors and that receives a command to perform at least one action with a test object, performs the at least one action with the test object, and returns test information indicative of at least one percept resulting from the at least one action;
   a data storage system that includes one or more tangible hardware memories and that contains an experience database containing data indicative of multiple classifications and, for each classification, at least one action that was performed with at least one previously-observed reference object having this classification, and at least one percept value that is based in whole or in part on the test information resulting from the at least one action; and
   a data processing system that includes one or more hardware processors and that:
   a) for each of multiple different classifications, computes or receives an initial prior probability that a test object falls within the classification;
   b) determines at least one action that should be performed with the test object to obtain at least one percept about the test object that is likely to enable the classification of the test object to be more accurately determined based on the initial prior probabilities and the data within the experience database;
   c) causes the object test system to perform the at least one action with the test object;
   d) receives test information from the object test system indicative of at least one percept resulting from the at least one action with the test object;
   e) computes at least one percept value;
   f) for each of multiple different classifications, determines a posterior probability that the test object falls within the classification based on the initial prior probability, the at least one percept value, and data within the experience database;
   g) determines whether any of the posterior probabilities meets or exceeds a threshold;
   h) if none of the posterior probabilities meet or exceed the threshold, repeats b) through i), substituting the posterior probabilities determined in f) for the initial prior probabilities in b); and
   i) when one or more of the posterior probabilities meets or exceeds the threshold, outputs information indicative of one or more of the classifications that correspond to the one or more posterior probabilities that meets or exceeds the threshold.

2. The object investigation and classification system of claim 1 wherein the data in the experience database includes data indicative of a distribution of percept values for at least one of the percepts resulting from an action that has been performed multiple times in association with a given classification or a given previously observed reference object.

3. The object investigation and classification system of claim 1 wherein the threshold is not the same during all of the repetitions of g).

4. The object investigation and classification system of claim 1 wherein the data processing system adds data about at least one of the percepts indicated by the received test information to the experience database.

5. The object investigation and classification system of claim 4 wherein the data processing system determines which of the percepts indicated by the received test information should have data about them added to the experience database based on the degree to which the at least one action that led to each percept caused a change in the probability that the test object has one or more of the classifications.

6. The object investigation and classification system of claim 1 wherein the data processing system determines if the percept values of at least one percept resulting from the at least one action performed with the test object is substantially unlike the percept values of the same at least one percept resulting from the same at least one action associated with any of the classifications described in the experience database.

7. The object investigation and classification system of claim 6 wherein the data processing system adds the percept values of at least one percept resulting from the at least one action with the test object to the experience database in association with a new classification that was not in the experience database when the data processing system determines that the percept values of at least one percept resulting from at least one action performed with the test object is substantially unlike the percept values of the same at least one percept resulting from the same at least one action associated with any of the classifications described in the experience database.

8. The object investigation and classification system of claim 7 wherein the data processing system determines at least one additional action to perform with the test object to obtain at least one percept associated with the at least one additional action and adds the percept value of the at least one percept resulting from the at least one additional action to the experience database.

9. The object investigation and classification system of claim 1 wherein the initial prior probabilities are the same.

10. The object investigation and classification system of claim 1 wherein the initial prior probabilities are weighted based on the number of times each classification has been associated with a previously-observed reference object in the experience database.

11. The object investigation and classification system of claim 1 wherein:
the experience database also contains data indicative of a time when each percept was obtained; and
the initial prior probabilities are weighted based on the time each percept was obtained.

12. The object investigation and classification system of claim 1 wherein:
the experience database also contains data indicative of a location where each percept was obtained; and
the initial prior probabilities are weighted based on the location each percept was obtained.

13. The object investigation and classification system of claim 1 wherein the determines at least one action that should be performed includes:
a) for each classification, computing a probability density function that describes a distribution of percept values expected for a percept resulting from an action that has been performed multiple times in association with the classification;
b) computing a degree to which two different probability density functions for two different classifications result in similar distributions of the percept values of the same percept when performing the same action;
c) multiplying the degree computed in 13b) by the prior probability that the test object has each classification used to compute the degree in 13b);
d) repeating 13b) and 13c) for all other possible pairs of classifications;
e) summing the results of all of the multiplications in 13c);
f) repeating 13a)-13e) for each of the other combinations of actions and percepts; and
g) selecting the action that yields the lowest summing value in 13e) for any percept as the action to be performed.

14. The object investigation and classification system of claim 13 wherein previously performed actions with the test object are given less preference in being re-selected as the action to be performed if the previously performed action was unsuccessful in producing percept values that help discriminate between the most likely classifications.

15. The object investigation and classification system of claim 1 wherein the object test system includes:

at least one controllable actuator that performs the at least one action with the test object; and
at least one tactile sensor that interacts with the test object and returns the test information indicative of at least one percept resulting from the at least one action.

16. The object investigation and classification system of claim 15 wherein the at least one action with the test object includes:
sliding across a surface of the test object; or
contacting the test object with a varying force.

17. The object investigation and classification system of claim 15 wherein the data processing system processes the test information indicative of the at least one percept is processed to indicate:
a type of surface texture on the test object;
a degree of roughness or smoothness of the test object;
a degree of coarseness or fineness of the test object;
a degree of hardness or softness of the test object;
a degree to which the test object has a springiness or dampens; or
a thermal property of the test object.

18. A non-transitory, tangible, hardware, computer-readable storage medium containing a program of instructions that cause a computer system that includes one or more processors running the program of instructions to perform the following functions in connection with an object test system that includes one or more actors and sensors and that receives a command to perform at least one action with a test object, performs the at least one action with the test object, and returns test information indicative of at least one percept resulting from the at least one action; and a data storage system that includes one or more tangible hardware memories and that contains an experience database containing data indicative of multiple classifications and, for each classification, at least one action that was performed with at least one previously-observed reference object having this classification, and at least one percept value that is based in whole or in part on the test information resulting from the at least one action:
a) for each of multiple different classifications, computes or receives an initial prior probability that a test object falls within the classification;
b) determines at least one action that should be performed with the test object to obtain at least one percept about the test object that is likely to enable the classification of the test object to be more accurately determined based on the initial prior probabilities and the data within the experience database;
c) causes the object test system to perform the at least one action with the test object;
d) receives test information from the object test system indicative of at least one percept resulting from the at least one action with the test object;
e) computes at least one percept value;
f) for each of multiple different classifications, determines a posterior probability that the test object falls within the classification based on the initial prior probability, the at least one percept value, and data within the experience database;
g) determines whether any of the posterior probabilities meets or exceeds a threshold;
h) if none of the posterior probabilities meet or exceed the threshold, repeats b) through i), substituting the posterior probabilities determined in f) for the initial prior probabilities in b); and
i) when one or more of the posterior probabilities meets or exceeds the threshold, outputs information indicative of one or more of the classifications that correspond to the one or more posterior probabilities that meets or exceeds the threshold.

19. The storage medium of claim 18 wherein the data in the experience database includes data indicative of a distribution of percept values for at least one of the percepts resulting from an action that has been performed multiple times in association with a given classification or a given previously observed reference object.

20. The storage medium of claim 18 wherein the threshold is not the same during all of the repetitions of g).

21. The storage medium of claim 18 wherein the program of instructions causes the computer system running the program of instructions to add data about at least one of the percepts indicated by the received test information to the experience database.

22. The storage medium of claim 21 wherein the program of instructions causes the computer system running the program of instructions to determine which of the percepts indicated by the received test information should have data about them added to the experience database based on the degree to which the at least one action that led to each percept caused a change in the probability that the test object has one or more of the classifications.

23. The storage medium of claim 18 wherein the program of instructions causes the computer system running the program of instructions to determine if the percept values of at least one percept resulting from the at least one action performed with the test object is substantially unlike the percept values of the same at least one percept resulting from the same at least one action associated with any of the classifications described in the experience database.

24. The storage medium of claim 23 wherein the program of instructions causes the computer system running the program of instructions to add the percept values of at least one percept resulting from the at least one action with the test object to the experience database in association with a new classification that was not in the experience database when the data processing system determines that the percept values of at least one percept resulting from at least one action performed with the test object is substantially unlike the percept values of the same at least one percept resulting from the same at least one action associated with any of the classifications described in the experience database.

25. The storage medium of claim 24 wherein the program of instructions causes the computer system running the program of instructions to determine at least one additional action to perform with the test object to obtain at least one percept associated with the at least one additional action and adds the percept value of the at least one percept resulting from the at least one additional action to the experience database.

26. The storage medium of claim 18 wherein the initial prior probabilities are the same.

27. The storage medium of claim 18 wherein the initial prior probabilities are weighted based on the number of times each classification has been associated with a previously-observed reference object in the experience database.

28. The storage medium of claim 18 wherein the experience database also contains data indicative of a time when each percept was obtained and the initial prior probabilities are weighted based on the time each percept was obtained.

29. The storage medium of claim 18 wherein the experience database also contains data indicative of a location where each percept was obtained and the initial prior probabilities are weighted based on the location each percept was obtained.

30. The storage medium of claim 18 wherein the determines at least one action that should be performed includes:
   a) for each classification, computing a probability density function that describes a distribution of percept values expected for a percept resulting from an action that has been performed multiple times in association with the classification;
   b) computing a degree to which two different probability density functions for two different classifications result in similar distributions of the percept values of the same percept when performing the same action;
   c) multiplying the degree computed in 30b) by the prior probability that the test object has each classification used to compute the degree in 30b);
   d) repeating 30b) and 30c) for all other possible pairs of classifications;
   e) summing the results of all of the multiplications in 30c);
   f) repeating 30a)-30e) for each of the other combinations of actions and percepts; and
   g) selecting the action that yields the lowest summing value in 30e) for any percept as the action to be performed.

31. The storage medium of claim 30 wherein previously performed actions with the test object are given less preference in being re-selected as the action to be performed if the previously performed action was unsuccessful in producing percept values that help discriminate between the most likely classifications.

32. The storage medium of claim 18 wherein the at least one action with the test object includes:
   sliding across a surface of the test object; or
   contacting the test object with a varying force.

33. The storage medium of claim 18 wherein the data processing system processes the test information indicative of the at least one percept is processed to indicate:
   a type of surface texture on the test object;
   a degree of roughness or smoothness of the test object;
   a degree of coarseness or fineness of the test object;
   a degree of hardness or softness of the test object;
   a degree to which the test object has a springiness or dampens; or
   a thermal property of the test object.

* * * * *